(12) United States Patent  
Murphy

(10) Patent No.: US 8,781,573 B2  
(45) Date of Patent: Jul. 15, 2014

(54) MULTI-FREQUENCY ELECTRICAL FIELD GENERATOR AND USE THEREOF

(76) Inventor: Patrick Murphy, Mississauga (CA)

( * ) Notice: Subject to any disclaimer, the term of this patent is extended or adjusted under 35 U.S.C. 154(b) by 317 days.

(21) Appl. No.: 11/214,714

(22) Filed: Aug. 31, 2005

(65) Prior Publication Data

US 2006/0047317 A1     Mar. 2, 2006

Related U.S. Application Data

(63) Continuation-in-part of application No. 10/929,455, filed on Aug. 31, 2004, now abandoned.

(51) Int. Cl.
*A61N 1/08*     (2006.01)

(52) U.S. Cl.
USPC ............................................. 607/2; 607/69

(58) Field of Classification Search
USPC .......................................... 607/69, 72, 76, 2
See application file for complete search history.

(56) References Cited

U.S. PATENT DOCUMENTS

| | | | |
|---|---|---|---|
| 4,237,898 A | | 12/1980 | Whalley |
| 4,266,533 A | | 5/1981 | Ryaby et al. |
| 4,911,686 A | | 3/1990 | Thaler |
| 5,634,939 A | | 6/1997 | Kuster |
| 5,658,322 A | | 8/1997 | Fleming |
| 5,690,692 A | * | 11/1997 | Fleming ................ 607/50 |
| 5,741,317 A | * | 4/1998 | Ostrow ................. 607/85 |
| 5,743,844 A | | 4/1998 | Tepper et al. |
| 5,817,142 A | | 10/1998 | Corder |
| 5,891,182 A | | 4/1999 | Fleming |
| 5,925,071 A | | 7/1999 | Story |
| 6,038,777 A | | 3/2000 | Cochran |
| 6,212,432 B1 | | 4/2001 | Matsuura |
| 6,235,251 B1 | | 5/2001 | Davidson |
| 6,304,782 B1 | | 10/2001 | Van Dick |
| 6,321,119 B1 | | 11/2001 | Kronberg |
| 6,321,120 B1 | | 11/2001 | Surbeck et al. |

(Continued)

FOREIGN PATENT DOCUMENTS

WO     WO9829156     7/1998

OTHER PUBLICATIONS

Gary Wade. "Rife Frequencies: finding the actual ultrasound frequencies to kill a microbe". Published Nov. 1, 1999. http://www.rifeenergymedicine.com/Alberta1.html.*

(Continued)

*Primary Examiner* — Eric D. Bertram
(74) *Attorney, Agent, or Firm* — Gerald A. Gowan; Gowan Intellectual Property

(57) ABSTRACT

An apparatus for the treatment of pathogens within a body comprising at least a pair of conductive electrodes adapted to conductively engage physically separated points on the body; and a signal generation device comprising signal-generating means for generating an oscillatory signal of a selected frequency which can range between a first frequency level and a second frequency level of greater than 1.0 MHz; means for causing said signal-generating means to step in frequency from said first frequency level to said second frequency level at predetermined frequency steps for predetermined intervals; and power transfer means, and preferably a power amplifier, responsive to said signal-generating means for supplying a voltage to said electrodes which voltage oscillates at said selected frequency. The output signal from the apparatus has a frequency range from 0.01 MHz to 660 MHz, and a preferred frequency range of 1.0 MHz and 5.4 MHz, has been found to provide greater flexibility in the treatment of pathogens.

15 Claims, 1 Drawing Sheet

(56) References Cited

U.S. PATENT DOCUMENTS

| | | | |
|---|---|---|---|
| 6,363,940 B1* | 4/2002 | Krag | 128/899 |
| 6,397,106 B1* | 5/2002 | DeBrouse | 607/69 |
| 6,678,558 B1 | 1/2004 | Dimmer et al. | |
| 6,684,108 B2 | 1/2004 | Surbeck et al. | |
| 2002/0156510 A1 | 10/2002 | Surbeck et al. | |
| 2002/0193833 A1 | 12/2002 | Dimmer et al. | |
| 2004/0049229 A1 | 3/2004 | Taricco | |
| 2005/0209640 A1* | 9/2005 | Palti | 607/2 |

OTHER PUBLICATIONS

Gary Wade. "Rife Frequencies: finding the actual ultrasound frequencies to kill a microbe". Published Nov. 1, 1999. http:llwww.rifeenergymedicine.comlAlbertal . html.*

Cheung et al. "Deep Local Hyperthermia for Cancer Therapy: External Electromagnetic and Ultrasound Techniques." Cancer Research. vol. 44, 4736s-4744s, Oct. 1984.*

Russian Patent Abstract RU21097273; Method of Information Extremely-High Frequency Effect Living Organism; Apr. 20, 1998; esp@cenet database—Worldwide.

Russian Patent Abstract RU2129419; Device for Detection of Pathologic Acupuncture Meridian (Versions); Apr. 27, 1999; esp@cenet database—Worldwide.

Russian Patent Abstract RU2179465; Physiotherapeutic Device; Feb. 20, 2002; esp@cenet database—Worldwide.

Thurlby Thandar Instruments—TGA1240 Series; Multi-channel Universal Waverform Generators; Thurlby Thandar Instruments Ltd.; Sep. 15, 2003.

Owner's Manual for the Pulseblaster—Intelligent General Purpose Pulse/Pattern Generation Board; SpinCore Technologies, Inc. ; Mar. 3, 2000.

"The Clark Zapper"—www.clarkzapper.com—5 pgs; Oct. 27, 2004.

"The Ultimate Zapper"—Printout from Internet—2pgs; Oct. 27, 2004.

"Welcome to www.clarkzapper.com"—www.huldaclark.com—3 pgs; Oct. 27, 2004.

"The Auto-Zap"—www.huldaclark.com—4 pgs; Oct. 27, 2004.

"www.SyncroZap.com"—www.huldaclark.com—4pgs; Oct. 27, 2004.

"Multi-Zap"—Printout from Internet—4pgs; Oct. 27, 2004.

Abstract for JP 2003-169855; Jun. 17, 2003; Nishide et al.

* cited by examiner

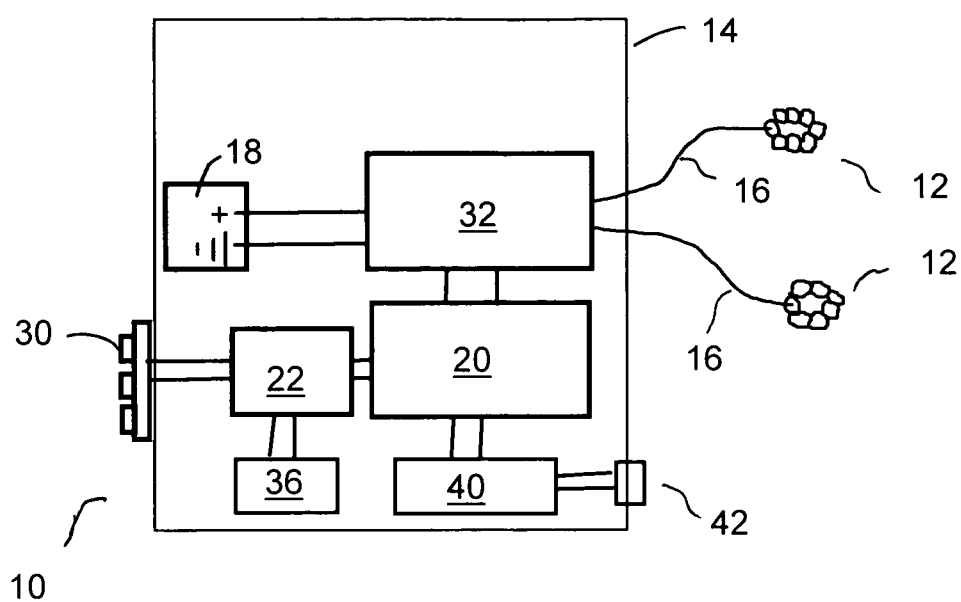

MULTI-FREQUENCY ELECTRICAL FIELD GENERATOR AND USE THEREOF

This application is a continuation-in-part of U.S. patent application Ser. No. 10/929455, filed Aug. 31, 2004, now abandoned.

FIELD OF THE INVENTION

The present invention relates to the field of electrical devices, and in particular, to a system, method and device for the treatment of various diseases, illnesses or pathogen-related illnesses by applying a low voltage electrical field of a range of electrical frequencies.

BACKGROUND OF THE INVENTION

It has been previously disclosed to use low voltage, electrical fields for inducing electrical signals in the tissue or cells of mammals, and that such signals have been proven to be effective in the treatment of various diseases, illnesses and illnesses caused by various pathogens.

In 1995 Dr. Hulda Clark published a book entitled "The Cure for all Diseases." It disclosed that the application of electrical energy at 30 kHz could succeed in killing viruses, bacteria, parasites, toxins and moulds.

In U.S. Pat. No. 5,690,692 a precise frequency synthesizer was disclosed for generating signals at 0.00004 Hz to 3 MHz as a square wave with a 50% duty cycle. The signal was purported to inactivate microorganisms and viruses in mammals. By subjecting a microorganism to a specific precise electrical frequency signal, it was possible to inactivate or kill the organism without effecting other microorganisms or tissues.

In U.S. Pat. No. 5,817,142, an electrical oscillator circuit for a similar purpose was disclosed, which utilized an oscillation frequency of between 100 and 900 kHz.

In U.S. Pat. No. 5,925,071, a device is described wherein a 9 volt electrical field is provided in which the frequency is stepped between 70 kHz and 880 kHz, in 1 kHz steps, with a brief respite period between each cycle.

In U.S. Pat. No. 6,304,782, viral induced physiological stress is reduced by electronic diagnosis and treatment is described wherein a patient is scanned with an electrical field that ranges from 2 kHz to 6 kHz.

These types of devices are known and used by many for the treatment of pathogens in the body. Commonly, these devices provide a small number of output frequencies, and the user selects one of the pre-set output frequencies. For example, several devices have two or 3 selected frequencies which might be used. However, each frequency is used one at a time, and the frequencies are usually less than 1.0 MHz, and are commonly less than or equal to the 30 kHz suggested by Dr. Clark.

When used for treatment, most devices apply a voltage to, or through, the user by having electrodes (or coils), held or attached at opposite extremities (e.g. in each hand, or on one ankle, and the opposite wrist). Typically, the frequency of the voltage applied is held at one frequency of 2.5 kHz or 30 kHz, and the voltage level (between the electrodes) is held at or below 1 volt.

While these devices have been used in the treatment of various diseases or illnesses, it would be beneficial to provide a device which will provide extended frequency ranges, in order to provide greater flexibility in the use of the device to treat pathogens. Further, it would be beneficial to provide an apparatus which could automatically cycle through a range of frequencies. Further, it would be beneficial to provide a device which is capable of applying a wider voltage range.

SUMMARY OF THE INVENTION

It has now been found that additional therapeutic benefits can be obtained by exposing the mammalian body, and in particular, a human, to low voltage fields having a variable frequency which extends up to 450 MHz, or more preferably, to a frequency level of up to 660 MHz. Further, in order to provide benefits from a wide range of frequencies, it would be desirable to provide a device which can provide a number of different frequencies in a single treatment stage. Even more preferably, it would be desirable to simultaneously apply treatment at a number of different frequencies.

In a further feature, it would be desirable to provide a device which could provide an audio indication which would be representative of the frequency being applied, so that the user can be provided with positive feedback on the operation of the device. This audio signal might also act to provide a sound therapy, or otherwise have a soothing effect on the user.

Accordingly, the present invention provides an apparatus for the treatment of pathogens within a body comprising:

at least a pair of conductive electrodes adapted to conductively engage physically separated points on the body; and a signal generation device comprising:

signal-generating means for generating an oscillatory signal of a selected frequency over a frequency range which frequency range can vary between a first frequency level and a second frequency level, and which second frequency level is greater than 1.0 MHz;

means for causing said signal-generating means to step in frequency from one frequency level to the other of said frequency levels in predetermined frequency steps, while holding each frequency level for a predetermined time interval; and power transfer means responsive to said signal-generating means for supplying a voltage to said electrodes which voltage oscillates at said selected frequency.

In a second aspect, the present invention provides the signal generation device described hereinabove.

In a third aspect, the present invention also provides a method for the treatment of pathogens with a mammal (either human or non-human) body, comprising attaching a pair of conductive electrodes to physically separated points on the body, connecting said electrodes to a signal generation device as described hereinabove, and operating said signal generation device so as to expose said body to an electrical field that ranges from said first frequency level to said second frequency level at predetermined frequency steps for predetermined intervals.

BRIEF DESCRIPTION OF THE DRAWINGS

Embodiments of this invention will now be described by way of example only in association with the accompanying FIGURE which FIGURE is a schematic representation of a device provided in accordance with the present invention.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example only. In the drawing, like reference numerals depict like elements.

It is expressly understood, however, that the drawing is for the purpose of illustration and description only and is not intended as a definition of the limits of the invention.

Referring to the FIGURE, an apparatus 10 for the treatment of pathogens within a body is shown. The body (not shown) is preferably a human body, but may be any mammalian body where treatment of pathogens is desirable.

The apparatus 10 preferably comprises a pair of electrodes 12 which are operatively connected to the body, and a signal generation device 14, which is shown as a schematic representation.

Electrodes 12 are each steel chain bracelets which are wrapped around the wrists of the user, and are connected to device 14 using a length of wire 16. While any suitable wire can be used, including coaxial cable or the like, the use of a single wire of a suitable wire gauge for this application, is preferred. Further, the length of each wire 16 is preferably essentially the same for both electrodes 12. Other types of electrodes might also be used, including for example, copper tubes, or other types of wrist straps or chains of various (preferably) conductive materials, which are meant to go around the wrists or ankles of the user. Alternatively, the electrodes may be held in place by attachment means such as tape, or releasable fasteners such as Velcro™ fasteners. The electrodes might also be electrodes specifically designed for attachment to the body, such as those electrodes which are used for EKG readings and the like. All of the electrodes might be used with or without electro-conductive creams or gels.

Typically, the electrodes will be in actual physical contact with the body (i.e. touching the body), however, this is not essential provided that an electrical field around or through the body can be established.

Further, select areas of the body might be used in order to provide enhanced performance, and or to assist in ensure that the voltage travels across, or otherwise through the body. For example, attachment of one electrode to the temple, or to the left upper lip area has been found to be of benefit in some applications, when used in combination with an electrode placed around the right ankle. Most commonly, however, the electrodes will be attached to each of the wrist Using wrist straps, which technique allows the user to perform other tasks while being treated.

The signal generation device 14 is connected to a power source which can include a battery 18, but might include an external power supply (such as a car battery, or the like), or to a transformer which is connected to an AC power supply. Any suitable power supply might, however, be used in this application.

The signal generation device 14 has a signal-generating means 20 which is preferably an integrated circuit, such as for example, a DDS (direct digital synthesis) chip designed to provide an output signal of the desired frequency, and which can be programmed, through a means for causing said signal generating means to step in frequency. Most preferably, this means for causing said signal generating means to step in frequency is preferably a programmable controller 22, which causes the DDS chip to provide a series of output frequencies. The DDS chip thereby provides a series of frequencies between the first and the second frequency level. Preferably, this range of frequency levels is between 0.001 and 660 MHz, more preferably between 0.001 and 450 MHz, still more preferably between 0.01 and 260 MHz, even more preferably between 0.2 and 150 MHz, and most preferably between 0.25 MHz and 100 MHz.

In any case, the upper (or second) frequency level is preferably greater than 1.0 MHz, preferably greater than 5.4 MHz, more preferably greater than 7.5 MHz, even more preferably greater than 10 MHz, and most preferably greater than 35 MHz.

As such, the preferred range of frequency levels is one where the first frequency level is 0.01 MHz or greater, and the second frequency level is between 5.4 MHz and 660 MHz, or more preferably between 5.4 MHz and 450 MHz. Still more preferably, the range of frequency levels is one where the first frequency level is 0.1 MHz, and the second frequency level is between 5.4 and 260 MHz. A most preferred frequency range, however, is one where the first frequency level is 1.0 MHz, and the second frequency level is 5.4 MHz.

However, the first frequency level can be established at any desired value. Typically, however, the first frequency level will be at or greater than 0.001 MHz.

For the purposes of this discussion, the first frequency level is typically any value lower than the second frequency level so that the frequency level will increase over time. However, the skilled artisan will readily appreciate that the frequency levels can be reversed so that the frequency applied decreases.

In this particular embodiment, the signal-generating means 20 is an AD9858 DDS chip available from Analog Devices, having a typical frequency output of up to 400 MHz. Other similar devices can also be used, depending on the desired application parameters. It is noted, thought, that the AD9858 DDS chip can be configured to provide frequencies of up to 450 MHz, and even extended to provide frequencies of up to 660 MHz.

Programmable controller 22, which in this example is a PIC16F870SS micro-controller chip, available from a number of manufacturers, but might be any suitable integrated circuit, is used to cause the output frequency to increase by steps. This might be used to create a very gradual increase, but preferably, the output frequency is caused to increase in a step change. The step change can be of any suitable size, but typically will be between 1 and 500 kHz, and more preferably, between 25 and 400 kHz. A most preferred step will be a change of 150 to 300 kHz.

Typically, the step change will result in an increase in the frequency level over time. However, the frequency level could start at a higher value and decrease in step changes.

The time, and order of application for each selected frequency can also vary but preferably the programmable controller 22 will merely increase the frequency from the first frequency level to the second frequency level by a step change in frequency. This step change will preferably occur in a regular time period of from 1 to 200 milliseconds, more preferably from 20 to 175 milliseconds, and most preferably from every 25 to 150 milliseconds.

The programmable controller 22 can be programmed to start at the first frequency level and increase the output frequency by the step change, and hold each output frequency for the desired time period, until the second frequency level. The programmable controller can optionally also be programmed to discontinue the application of the electrical field to the body for a selected respite period. The respite period can vary in time from between 2 and 60 minutes, and after the respite period, programmable controller 22 will again enable the system so as to apply the output frequency to the body through electrodes 12.

Preferably, however, the selected frequency treatment range is applied in a single application without using any respite periods.

The programmable controller can also be used to simultaneously provide a series of frequencies in order to reduce the application time, and/or provide a more effective treatment regiment. As such, in a preferred feature, the programmable controller simultaneously provides at least two output frequencies, at least one of which meets the frequency criteria established hereinabove. Preferably between 2 and 10 treatment frequencies are simultaneously applied, and more preferably between 3 and 6 treatment frequencies are simultaneously applied.

Preferably, all of the simultaneously applied frequencies meet the frequency criteria established hereinabove. One DDS chip can be used to provide this multi-frequency functionality, or a series of DDS chips can be used.

Further, the programmable controller can also be used to avoid the output of any frequencies which are undesirable. For example, if a frequency range of say 5.4 MHz to 35 MHz is found to be unnecessary or undesirable for application to a particular body, the programmable controller can be programmed to by-pass this output signal range.

Accordingly, the programmable controller 22 can be pre-programmed with respect to the number of treatment periods to be applied, the first and second frequency levels to be used, the timing and number of frequency step changes, the timing of any programmed changes to the treatment regime, or the length of the respite period(s), or any of the other controllable features of the device. These aspects can be preprogrammed prior to installation of the programmable controller into device 14, or can be programmed, in situ, by the vendor, or device operator through various input devices, including for example, input devices, such as a touch sensitive display, or keyboard 30, on device 14. Further, the programmable controller may contain pre-set programs that control all aspects or features of the treatment regime.

The programmable controller might also be connectable to external programming means such as a computer, a PDA, or the like, in which the programming parameters might be selected or changed.

The programs can be saved in a memory chip, 36, such as a 24LC256 memory chip.

The signal from the signal generation means is preferably transferred to the electrodes using a power transfer means which can increase the available voltage and/or the available current. In the FIGURE power amplifier 32 increases the voltage from an output signal of 0.5 volts to 2.5 volts. However, the actual voltages used can vary depending on the nature of the body to be treated, the frequency ranges selected, and/or the pathogen to be treated. Typically, however, the voltage between the electrodes will preferably be less than 25 volts, more preferably less than 10 volts, and even more preferably less than 6 volts. Those skilled in the art will be readily able to determine suitable voltages for use for a particular body and/or pathogen to be treated, and provide an amplifier capable of providing the desired output voltages. A preferred minimum voltage would be any voltage greater than 0.1 volts.

The user and/or programmable controller might also be provided with control of the output level so as to adjust the power amplifier output intensity. In this fashion, the output intensity for a user might, for example, be increased over a series of programmed treatments.

The output signal, preferably is, or simulates an alternating current signal. In a preferred feature, the power transfer means is used to split the signal so that positive signals are sent to one electrode, while negative signals are sent to the other electrode. In this fashion, the apparent voltage differential between the electrodes is increased.

The device 14 can also be fitted with various displays, lights and the like, in order to provide an indication of the status of the device. This could include a timer to show, for example, the time remaining in a treatment or respite period, or the like. The skilled artisan would be aware of the type of information which might be presented in this fashion.

In particular, however, an audio generator 40 is provided that is connected to signal-generating means 20 so as to provide an audio output which corresponds to, but is not equal to, the applied frequency. For example, an audio range of between 200 Hz and 3000 Hz can be selected to represent the applied frequency range of for example, 5.4 MHz to 100 MHz. As such, as the treatment frequency is being applied by device 14, the user will hear an audio output, through output jack 42, which can be connected to, for example, a speaker (not shown), or headphones (not shown).

This audio output provides positive feedback to the user that the device is operating correctly, in that the frequency is increasing (for example), and can provide a soothing effect on the user. As such, the audio output provides an additional feature of providing sound therapy to the user.

Thus, it is apparent that there has been provided, in accordance with the present invention, an apparatus and method for the treatment of pathogens within a body, which fully satisfies the goals, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

Additionally, for clarity and unless otherwise stated, the word "comprise" and variations of the word such as "comprising" and "comprises", when used in the description and claims of the present specification, is not intended to exclude other additives, components, integers or steps.

Moreover, the words "substantially" or "essentially", when used with an adjective or adverb is intended to enhance the scope of the particular characteristic; e.g., substantially planar is intended to mean planar, nearly planar and/or exhibiting characteristics associated with a planar element.

Further, use of the terms "he", "him", or "his", is not intended to be specifically directed to persons of the masculine gender, and could easily be read as "she", "her", or "hers", respectively.

Also, while this discussion has addressed prior art known to the inventor, it is not an admission that all art discussed is citable against the present application.

I claim:

1. A method for the treatment of pathogens within a mammal body, comprising: attaching a pair of conductive electrodes to physically separated points on the body; connecting said electrodes to a signal generation device, which device comprises:

signal-generating means for simultaneously generating at least two different varying oscillatory signals of selected frequency ranges which frequency ranges can vary between a first frequency level of at least 5.4 MHz and a second frequency level of up to 660 MHz;

means for causing said signal-generating means to step in frequency from said first frequency level to said second frequency level, at predetermined frequency steps of equivalent frequency values, so that each of said frequency ranges increase in said regular steps, and holding each frequency level for both frequency ranges for a predetermined time interval; and power transfer means responsive to said signal-generating means for supplying an output voltage to said electrodes, which voltage oscillates at each of said selected frequencies; and operating said signal generation device so as to expose said body to an electrical field that ranges from said first frequency level to said second frequency level at predetermined frequency steps for predetermined intervals, and which voltage is less than 25 volts.

2. A method as claimed in claim 1 wherein at least one conductive electrode is adapted to be connected to the body at the temple or at the upper lip region.

3. A method as claimed in claim 1 wherein said electrodes are adapted to be connected to the wrists of the body using wrist straps.

4. A method as claimed in claim 1 wherein each of said electrodes are connected to said signal generation device using single wires, and the single wires to each electrode have the same length.

5. A method as claimed in claim 1 wherein said signal-generating means is an integrated circuit.

6. A method as claimed in claim 5 wherein said integrated circuit is a DDS (direct digital synthesis) chip designed to provide an output signal of the desired frequency.

7. A method as claimed in claim 1 wherein each of said frequency steps is a frequency change of between 1 and 500 kHz.

8. A method as claimed in claim 7 wherein each of said frequency steps is a frequency change of between 150 and 300 kHz.

9. A method as claimed in claim 1 wherein said frequency steps occur in a time period of between 1 to 200 milliseconds.

10. A method as claimed in claim 1 wherein said means for causing said signal-generating means to step in frequency is a programmable controller, and said programmable controller can be preprogram with respect to frequency levels, step changes, timing of changes, or respite periods, prior to installation, or can be programmed through an input device.

11. A method as claimed in claim 10 wherein said programmable controller is programmed by connecting to an external programming means.

12. A method as claimed in claim 11 wherein said external programming means is a computer, or a PDA.

13. A method as claimed in claim 1 wherein between 3 and 6 different output frequencies are simultaneously provided.

14. A method as claimed in claim 1 wherein said power transfer means is a power amplifier.

15. A method as claimed in claim 1 wherein said signal generation device additionally comprises an audio output means which audio output means provides an audio signal which varies according to the output frequencies so as to be indicative of the frequencies of the output signal from said signal-generating means.

\* \* \* \* \*